United States Patent [19]

von der Goltz

[11] Patent Number: 5,051,239

[45] Date of Patent: Sep. 24, 1991

[54] FLOW DEVICE FOR USE IN HEMORRHAGING TIME MEASURING APPARATUS AND METHOD OF MEASURING A HEMORRHAGING

[76] Inventor: Volker F. von der Goltz, Michael-Haydn-Weg 1, D-8221 Seeon, Fed. Rep. of Germany

[21] Appl. No.: 272,944

[22] Filed: Nov. 18, 1988

[30] Foreign Application Priority Data

Nov. 19, 1987 [DE] Fed. Rep. of Germany ....... 3739247
Oct. 19, 1988 [EP] European Pat. Off. ......... 88117388.4

[51] Int. Cl.$^5$ ............................................. G01N 33/86
[52] U.S. Cl. ....................................... 422/73; 73/64.1; 436/69
[58] Field of Search ..................... 422/73, 81, 99, 100, 422/102; 436/63, 69; 73/64.1

[56] References Cited

U.S. PATENT DOCUMENTS 3,900,290 8/1975 Hornstra ............................ 73/64.1
4,604,894 8/1986 Kratzer et al. ........................ 422/73
4,780,418 10/1988 Kratzer ................................. 436/69

Primary Examiner—W. Gary Jones
Attorney, Agent, or Firm—Fleit, Jacobson, Cohn, Price, Holman & Stern

[57] ABSTRACT

A flow device for use in a hemorrhaging time measuring apparatus comprises a housing through which the blood to be tested flows under a suction effect. In its interior the housing has a separating wall which is arranged transversely with respect to the direction of flow of the blood through the housing and which has at least one aperture therein. Disposed upstream of the aperture is a suction tube for sucking the blood through the housing. The suction tube extends into a cavity within the housing which is upstream of the aperture in the separating wall, with the downstream end of the tube disposed in the vicinity of the aperture. The blood is sucked into the device under a constant suction effect and thrombus formation takes place in the region of the aperture.

21 Claims, 2 Drawing Sheets

FLOW DEVICE FOR USE IN HEMORRHAGING TIME MEASURING APPARATUS AND METHOD OF MEASURING A HEMORRHAGING

BACKGROUND OF THE INVENTION

Various forms of flow device are used for carrying a flow of blood in an apparatus for measuring the blood hemorrhaging time. Thus, the apparatus for measuring hemorrhaging time in vitro, as disclosed in German laid-open application (DE-OS) No. 32 47 810, uses a through-flow device having a separating wall in the form of a porous member with an aperture therein. The porous member is supported on a support structure which is not permeable to air, and is of such a design configuration that blood passes only through the aperture therein, and cannot flow round the sides of the porous member. That provides an apparatus, and therewith a method, for measuring hemorrhaging time in vitro, in which it is possible to simulate the hemorrhaging processes under in-vivo conditions.

In another form of hemorrhaging time measuring method, as disclosed in German laid-open application (DE-OS) No. 35 41 057, the blood to be tested is sucked into a capillary tube under a given reference suction force which is produced with a control feedback, wherein the amount of blood flowing in the capillary is ascertained as a measurement in respect of aggregation or coagulation of the thrombocytes. That arrangement also makes it possible accurately to simulate hemorrhaging processes under in-vivo conditions.

SUMMARY OF THE INVENTION

An object of the invention is to provide a flow device for use in a hemorrhaging time measuring apparatus, which can not only accurately simulate in-vivo conditions but which also provides for a high level of reproducibility of the measurement results.

Another object of the present invention is to provide a flow device for use in a hemorrhaging time measuring apparatus, which is of a simple construction and reliable in operation while affording the option of a wide range of operating procedures.

Still another object of the present invention is to provide a method of measuring blood hemorrhaging time under simulated in-vivo conditions with a high degree of measurement result reproducibility.

Yet a further object of the present invention is to provide a blood hemorrhaging time measuring method which can be carried out in a simple and rational manner with a wide range of operating materials.

In accordance with the present invention, these and other objects are achieved by a flow device for use in a hemorrhaging time measuring apparatus, wherein the flow device comprises a housing through which the blood to be tested flows, passing through at least one aperture within the housing. A receiving means is disposed downstream of the aperture, for receiving the blood which has flowed therethrough and a suction tube is arranged upstream of the aperture. The suction tube projects into a cavity in the housing, which is disposed upstream of the aperture and which air-tightly surrounds the aperture, with the downstream end of the suction tube being disposed in the vicinity of the aperture. The downstream end of the suction tube is disposed at such a spacing from the aperture that, with a given suction effect, thrombus formation occurs in the aperture.

In the method aspect of the invention, a method of measuring blood hemorrhaging time, in particular in the first phase of thrombocyte aggregation, provides that the blood to be tested is sucked under a given suction force through the suction tube of the above-defined flow device, and the amount of blood which flows through the suction tube is measured. Thrombus formation is produced at the aperture in the device.

It will be seen therefore that the construction of the flow device and the method in accordance with the principles of the present invention ensure that thrombus formation takes place at a precisely defined location in the device, that is to say at the aperture which is provided in the housing, for example in a wall portion of the housing or in a separating or partitioning wall which defines the cavity in the housing, into which the suction tube projects. In that way, it is possible to produce precisely reproducible measurement results in respect of thrombocyte aggregation, in particular in the first phase thereof, while also accurately simulating the in-vivo conditions in respect of the hemorrhaging process. The range of variation attained in the measurement results has been found to be below 5%, thus satisfying the requirements generally made in respect of clinical and scientific uses.

In a preferred embodiment of the invention the at least one aperture is provided in a partitioning or separating wall which is of a pressure-tight nature and which is pressure-tightly connected to the housing on the interior thereof, to define the cavity into which the suction tube projects. The separating wall may be in the form of a porous member, with a pore size of less than 5 $\mu$m and larger than 0.01 $\mu$m, with an aperture therein. The diameter of the aperture may be between about 50 and 300 $\mu$m, preferably between 150 and 250 $\mu$m. The porous member may be permeated and/or coated with for example collagen.

However, it is also possible for the separating wall to be made from a non-porous material, for example a plastic plate member, which is coated with collagen in particular in the region of the aperture therethrough. It is also possible for the separating wall to be made from a plastic foil which is suitably supported in the housing by a support disc or other support structure. The plastic disc may also be in the form of a portion of artificial skin, as is known for example as a skin implant from U.S. Pat. No. 4,458,678. It is further possible to use a separating wall consisting of a plastic plate or a plastic foil comprising a polymerised compound on an acrylic acid base, as is disclosed for example in U.S. Pat. No. 4,451,568, and to which the collagen is bonded covalently, for example by way of an oxiran group or groups. A suitable material for the separating wall member is also cellulose acetate which is coated with collagen. Instead of collagen it would also be possible to use another agent which induces thrombocyte aggregation, for example adenosine diphosphate, or a thrombocyte-activating agent, for example PAF which is a phospholipid (see Römpps Chemie-Lexikon, 8th edition, pages 3159 and 3160), such materials being used to provide a coating on the separating wall at least in the region of the aperture therethough.

The diameter of the aperture may be from about 20 $\mu$m to 500 $\mu$m, like also the inside diameter of the suction tube. The inside diameter of the suction tube is preferably from about 150 to 250 $\mu$m.

In use of the flow device in accordance with the invention, it is advantageous to operate with a given constant suction force with which the blood is sucked through the suction tube and through the aperture, then measuring the variation in respect of time of the amount of blood flowing through the device. For that purpose it is possible for example to make use of the above-discussed method disclosed in German laid-open application (DE-OS) No. 35 41 057.

The addition of agents which influence the hemorrhaging processes, to the blood to be tested, also makes it possible to obtain certain diagnostic indications or indications in respect of pharmacological influences on the blood, for example thrombocyte adhesion or aggregation, as for example by pain-killing agents, sleeping drugs or the like. Those agents may involve for example a coagulation-inhibiting agent such as heparin, Na-citrate and coumarin derivatives, or thrombocyte aggregation-inhibiting agents such as for example acetyl salicylic acid, sulfinpyrazone or ticlopidin, or a thrombocyte aggregation-inducing agent such as for example adenosine diphosphate, PAF, collagen or ristocetin. In that connection it is also possible to carry out a plurality of measuring operations in which the procedures are performed with or without the specified agents for affecting hemorrhaging, in order then to arrive at the required diagnostic indications from the different measurement results produced.

For example it is possible to prove the v.Willebrand syndrome, in the following fashion. That syndrome is to be attributed to a reduced level of adhesion capability of the blood platelets, so that a retarded drop in the amount of blood flowing through the device can be found in the measurement operation. If in a subsequent measuring run ristocetin is added to the blood, it is found that that retarded drop in the flow of blood, which results from the thrombus formation phenomenon, no longer occurs.

The apparatus may be put to a further use for example in relation to rheological blood investigations (hemorrheology) or in determining the viscosity of blood. For that purpose, the respective amounts of blood flowing through the device may be measured while maintaining a constant suction pressure acting thereon at different points of time.

It is also possible to apply varying pressures for transporting the blood through the suction tube, then determining the respective amounts of blood flowing through the device. It is also possible to apply pulsating suction pressures for transporting the blood.

For carrying out such rheological blood tests or operations for determining the viscosity of blood, it is also possible to employ a device which does not have the above-mentioned partitioning or separating wall with the aperture therethrough, that is to say a device in which a storage vessel in which the blood to be tested is contained is connected to the receiving vessel by way of the suction tube, wherein the required suction force for sucking the blood through the device is produced for example by way of an opening in the receiving container, or the above-mentioned varying pressures or pulsating pressures are applied to the suction tube by way of the opening in the receiving container.

By way of example, the following diagnostic indications may be obtained:

Disturbances in primary hemostasis, pre- or postoperative monitoring of thombocyte function, testing of the thrombocyte function in stored blood, measurement of the thrombocyte function in thrombocytopenia (leucosis), measurement of the thrombocyte function in infants and children, measurement of the pharmacological influencing of thrombocyte adhesion and aggregation, measurement of the thrombocyte function in bone marrow transplant operations, testing of primary hemostasis after burn injuries, reduced thrombocyte adhesion, reduced thrombocyte aggregation, thrombocyte function after the administration of DDAVP, and determining the viscosity of blood.

Further objects, features and advantages of the device and method according to the present invention will be more clearly apparent from the following description of preferred embodiments thereof.

DESCRIPTION OF THE PREFERRED EMBODIMENTS

Figure 1:
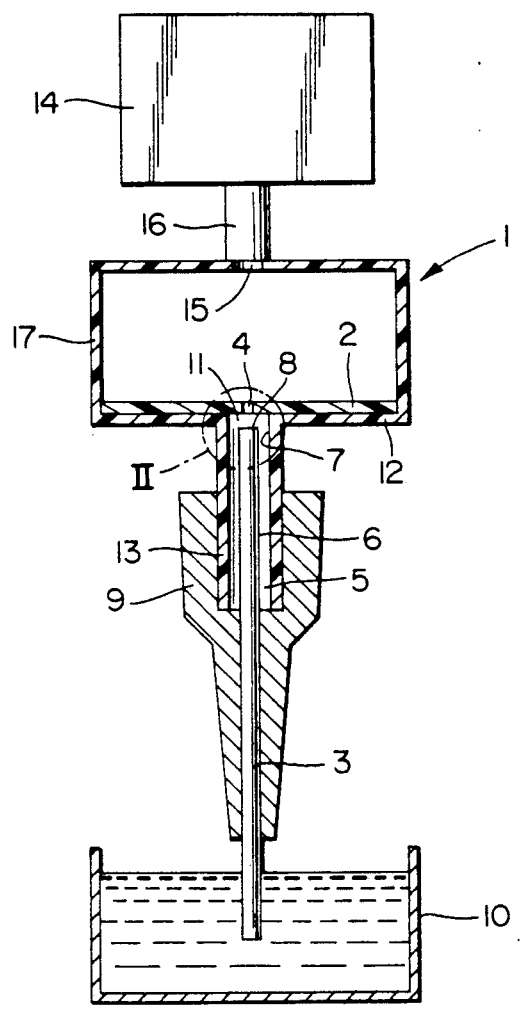
FIG. 1 is a diagammatic view of an embodiment of a flow device according to the present invention.

Referring firstly to FIG. 1, a flow device 1 as illustrated therein, in accordance with the principles of the present invention, comprises housing portions 17 and 9 having configurations thereon such that the housing portions 17 and 9 can be fitted together in the illustrated position, as will be described below. The housing portion 17 is substantially in the form of a receiving container for receiving blood which has flowed through the device 1, being of a volume which approximately corresponds to the volume that the blood to be tested occupies in a supply container as indicated at 10 in FIG. 1. Provided at the bottom of the housing portion 17 is a wall portion, in the form as illustrated of a separating wall 2, which has an aperture 4 therein. The separating wall 2 may be of a porous nature, as described in above-mentioned German specification No. 32 47 815, or it may be in the form of a non-porous plastic plate which is coated with for example collagen more particularly in the region of the aperture 4 or in its entirety. The separating wall 2 which is of a pressure-tight nature and which is pressure-tightly fitted at its peripheral edge to the wall of the housing portion 17 lies on the bottom part 12 of the housing portion 17. The separating wall 2 may additionally be supported by a support structure (not shown) which is arranged above the separating wall and which bears against the top surface of the separating wall 2. The bottom 12 of the housing portion 17 has an opening 11 therethrough, which surrounds the aperture 4 in the separating wall 2. As stated above, the separating wall 2 lies in a pressure-tight condition on the bottom 12 of the housing portion 17.

Figure 2:
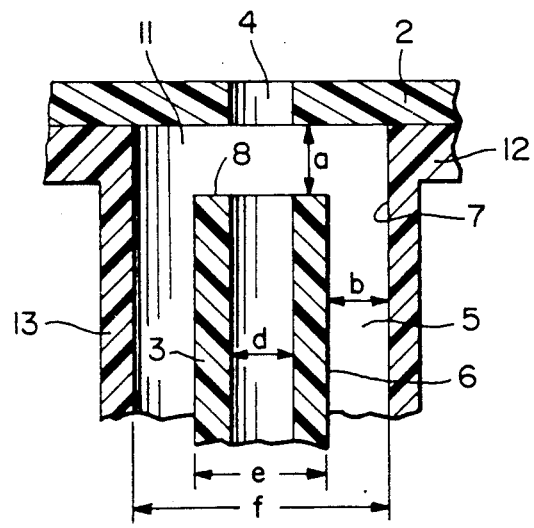
FIG. 2 is a cut-away view of part of the FIG. 1 device.

Referring now in addition to FIG. 2, it will be seen therefrom that the opening 11 in the bottom 12 of the housing portion 17 of the flow device 1 is surrounded by an inner wall 7 which is the inner wall of a tube portion 13 formed on the bottom 12 on the outside thereof, that is to say extending downwardly from the bottom 12 in the position of the device as shown in FIG. 1. The tube portion 13 is fitted into a receiving bore of suitable configuration in the housing portion 9, as can be clearly seen from FIG. 1. The outside diameter of the tube portion 13 is matched to the inside diameter of the receiving bore in the housing portion 9, thus providing a snug press fit between the two components.

The flow device 1 further includes a suction tube 3 through which the blood to be tested and investigated is sucked from the supply container 10. The suction tube 3, with its bore therethrough, forms the hemodynamic resistance. The tube 3 is fixedly inserted into a through bore in the housing portion 9 and projects into the space defined in the housing portion 17 of the device 1, which is surrounded by the inside wall 7 of the tube portion 13. In that arrangement there is a space 5 between the wall 7 and the peripheral surface 6 of the suction tube 3. The provision of the space 5 ensures that the upper part of the suction tube 3 can be loosely introduced into the space defined by the tube portion 13. The spacing of the peripheral surface 6 of the suction tube 3 from the wall 7 which extends at least substantially parallel thereto may be up to 1.0 mm, more particularly 0.5 mm. That spacing is indicated at reference letter b in FIG. 2. The spacing b ensures that the suction tube 3 can be satisfactorily fitted into the tube portion 13, taking account of tolerances which may occur. The spacing b may also be such that in the measuring operation, no blood can pass into the space 5 between the wall 7 of the tube portion 13 and the peripheral surface 6 of the suction tube 3.

The inside diameter of the suction tube 3, as indicated at d in FIG. 2, may be from about 20 to 500 $\mu$m, preferably from 150 to 250 $\mu$m. The suction tube 3 may comprise any suitable material, preferably polytetrafluoroethylene.

The suction tube 3 is so arranged and positioned that the downstream end 8 thereof is disposed in the vicinity of the aperture 4 through the separating wall 2. The spacing of the end 8 of the suction tube 3 from the underneath edge of the aperture 4, as indicated at a in FIG. 2, is from 0.1 to 6.0 mm. The outside diameter of the suction tube 3, as indicated at e in FIG. 2, is such as to ensure adequate mechanical stability, and may be from 0.05 to 1.5 mm, preferably 1.0 mm. The inside diameter of the space enclosed by the wall 7, as indicated at f in FIG. 2, also depends on the outside diameter e of the suction tube 3, for the above-indicated reasons, and in the illustrated embodiment may be from 1.5 to 2.5 mm, preferably 2.0 mm.

For the purposes of measuring the hemorrhaging process in respect of the blood to be tested, the blood is sucked out of the container 10 through the suction tube 3 by means of a suction and measuring device 14. For that purpose, a suitable reduced pressure is produced in the interior of the housing portion 17 which is communicated with the suction and measuring device 14 by way of an opening 15 in the upper wall part of the housing portion 17, and a suction tube 16 which connects the housing portion 17 to the device 14. That reduced pressure is also to be found upstream of the aperture 4 in the space which is enclosed by the wall 7 and into which the suction tube 3 extends. That reduced pressure also occurs in the through-flow bore or capillary passage in the suction tube 3. That is ensured by virtue of the fact that the tube portion 13 which pressure-tightly surrounds the aperture 4 at the underside of the separating wall 2 is also pressure-tightly fitted into the corresponding bore or recess accommodating same in the lower housing portion 9.

The suction and measuring device 14 operates in such a way that in the measurement operation, a constant suction force or pressure is maintained by way of the suction tube 16, as far as the through bore of the suction tube 3, whereby the constant suction pressure is applied to the blood which is to be drawn up into the suction tube 3 from the container 10. The suction and measuring device may be of any suitable construction, being for example of the kind disclosed in above-mentioned German laid-open application (DE-OS) No 35 41 057.

During the measurement operation, the blood gradually forms a plug in the region of the aperture 4, in particular in the area around the aperture at the underside of the separating wall 2 and extending into the aperture 4, by virtue of aggregation of the thrombocytes. That plug finally entirely closes off the aperture 4. Blood which flows away laterally towards the wall 7 is deposited in the region formed by the spacing a of the end 8 of the suction tube 3 from the underneath surface of the separating wall 2. It has been found that, when the dimensions of the structure are suitably selected, the device ensures that no blood penetrates between the peripheral surface 6 of the suction tube 3 and the oppositely disposed part of the wall 7. It has also been found that thrombus formation always occurs in a reproducible fashion at the aperture 4. That therefore affords a high level of reproducibility of the measurement results and thus provides accurate information about the hemorrhaging process, in particular concerning thrombocyte aggregation in the first phase.

Figure 3:
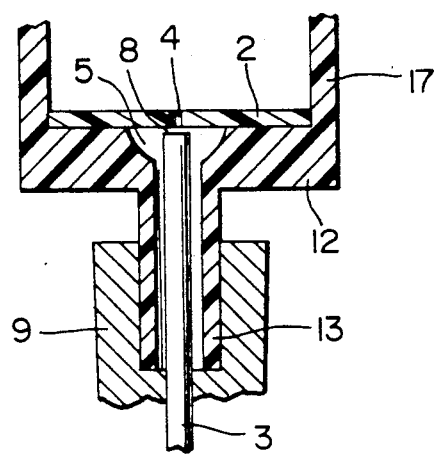
FIG. 3 shows a further embodiment of the flow device according to the invention.

Reference will now be made to the embodiment of the flow device according to the invention as shown in FIG. 3. That device is generally similar to the device shown in FIGS. 1 and 2 and it will therefore not be described in detail again at this stage, for that reason. It will be seen from FIG. 3 however that the space 5 around the aperture 4 in the separating wall 2, being the space into which the upper end 8 of the suction tube 3 projects, is enlarged relative to the remainder of the space defined between the suction tube 3 and the wall structure surrounding it, in the region of the end 8 of the suction tube.

Figure 4:
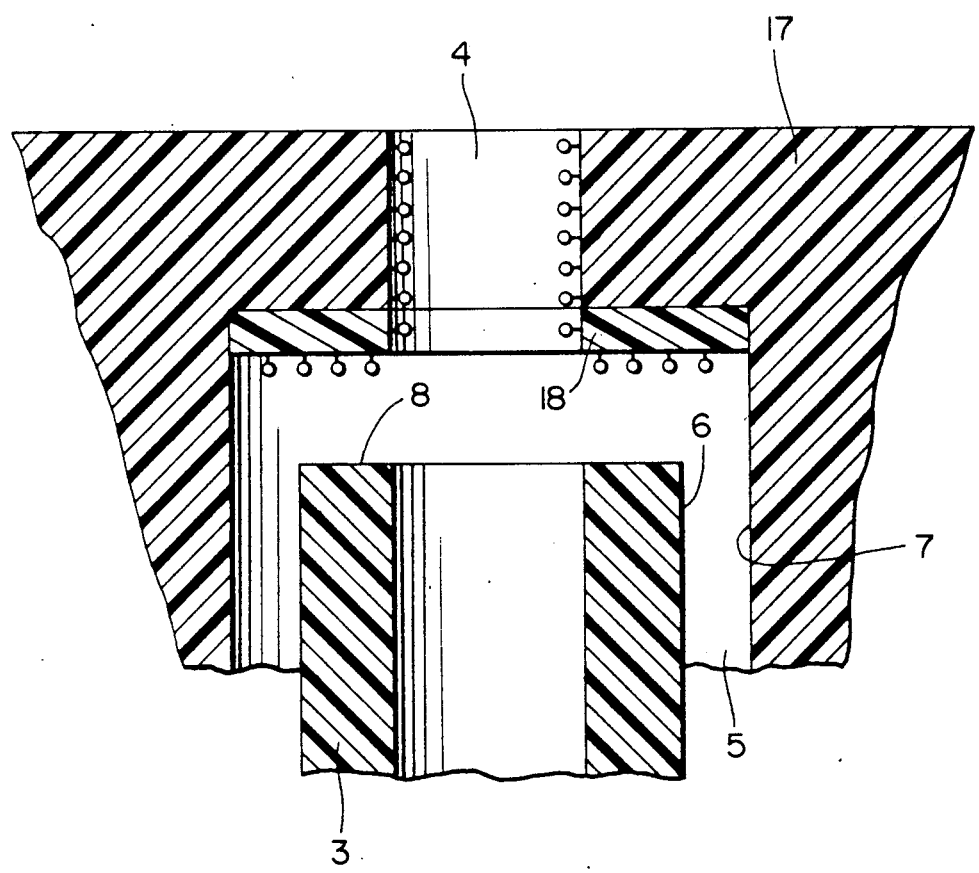
FIG. 4 is a view on an enlarged scale of the area around the aperture in the flow device of a third embodiment of the present invention.

In the case of the illustrated embodiments of the flow device according to the invention, it is also possible for the wall portion which forms the separating wall 2 to be formed in one piece with the housing portion 17. Such a construction may be for example of the configuration shown in FIG. 4. In that construction, the aperture 4 is formed directly in the bottom part of the housing portion 17. The space 5 which surrounds the aperture 4 and which is enclosed by the wall 7 is also formed in or at the bottom of the housing portion 17. Thus, the upper end 8 of the suction tube 3 extends into the space 5 formed in the bottom of the housing portion 17, in the manner shown in FIG. 4. At least the region which is disposed around the aperture 4 and which is towards the end 8 of the suction tube 3 is provided with a coating or layer as indicated at 18 which is formed from a thrombocyte aggregation-inducing agent or a thrombocyte-activating factor, as referred to hereinbefore.

When carrying out a measuring operation with the flow device according to the present invention, a flushing agent such as for example a NaCl-solution or albumen is deposited in the region between the end 8 of the suction tube and the aperture 4, laterally of the aperture 4, without passing into the space between the wall 7 and the peripheral surface 6 of the suction tube 3. The blood which then follows on flows through the aperture 4 and adhesion of the thrombocytes causes thrombocytes to adhere in the region of the aperture 4, with the result that a thrombus is formed, resulting in the aperture 4 being closed.

If the flow device according to the invention is to be used for rheological blood investigations, for example and more particularly operations for measuring the viscosity of blood, the aperture 4 may also be omitted so that the tube 3 is directly connected to the receiving space defined by the housing portion 17.

The separating wall material may comprise extra-cellular matrix which itself has thrombocyte aggregation-inducing properties or which is additionally provided with a thrombocyte aggregation-inducing agent. The material of the separating wall may also consist of a shaped body of collagen material. Animal skin is also suitable as a material for the separating wall.

If the device according to the invention is to be used for the above-mentioned diagnostic indications, the agents which influence the hemorrhaging procedures may also be added to the blood to be tested, by way of the material of the separating wall 2. For that purpose the substance or substances involved, which is or are selected in dependence on a given diagnosis to be carried out in the measurement operation, may also be incorporated into the material of the separating wall, which for that purpose is in particular of a porous nature. The substance or substances is or are then added to the blood from the material of the separating wall during the measuring operation.

It will be appreciated that the above-described devices and methods according to the principles of the present invention have been described solely by way of example and illustration of the invention and that various other modifications and alterations may be made therein without thereby departing from the spirit and scope of the invention.

I claim:

1. A flow device for use in a hemorrhaging time measuring apparatus comprising: a flow housing providing at least one aperture through which blood to be measured flows the housing defining a space air-tightly surrounding the aperture upstream thereof; a receiving means disposed downstream of said aperture to receive the blood which has flowed therethrough; and a suction tube adapted to carry a suction-induced flow of blood towards said aperture and arranged upstream of aperture and projecting into said space around the aperture upstream thereof, the downstream end of the suction tube being disposed in the vicinity of the aperture at such a spacing from the aperture that, with a given suction pressure, thrombus formation occurs in the aperture and including an intermediate space between at least a portion of the peripheral surface of the suction tube, which portion directly adjoins said downstream end of the suction tube, and a wall portion of the housing.

2. A device as set forth in claim 1 wherein said aperture is provided in a seaparating wall means of a pressure-tight nature and pressure-tightly connected to the inside of the housing.

3. A device as set forth in claim 2 wherein said separating wall means is made from a plastic material with bonding-active groups at the surface thereof, for covalently bonding collagen.

4. A device as set forth in claim 3 wherein said plastic material includes an oxiran group.

5. A device as set forth in claim 2 wherein said separating wall means comprises extra-cellular matrix including an agent for inducing thrombocyte aggregation.

6. A device as set forth in claim 2 wherein said separating wall means comprises a shaped body of collagen material.

7. A device as set forth in claim 2 wherein said separating wall means comprises animal skin.

8. A device as set forth in claim 2 wherein said separating wall means comprises a plastic material which induces thrombocyte aggregation.

9. A device as set forth in claim 1 wherein at least a region around said aperture is coated with an agent for inducing thrombocyte aggregation.

10. A device as set forth in claim 1 wherein at least a region around said aperture is coated with a thrombocyte-activating factor.

11. A device as set forth in claim 1 wherein said suction tube is of an inside diameter of from 20 to 500 $\mu$m.

12. A device as set forth in claim 11 wherein said inside diameter is from 150 to 250 $\mu$m.

13. A device as set forth in claim 1 wherein said spacing of said downstream end of said suction tube relative to said aperture is from 0.1 to 6.0 mm.

14. A device as set forth in claim 13 wherein said spacing is approximately 2.0 mm.

15. A device as set forth in claim 1 wherein said housing includes a wall portion of tubular configuration which pressure-tightly surrounds said aperture, and wherein said suction tube is inserted into said tubular wall portion.

16. A device as set forth in claim 15 wherein said housing comprises first and second housing portions, said first housing portion includes said tubular wall portion, and said suction tube is fixed in said second housing portion.

17. A device as set forth in claim 1 wherein at least parts thereof are in the form of disposable parts.

18. A device as set forth in claim 1 which is in the form of a disposable device.

19. A flow device for use in a hemorrhaging time measuring apparatus comprising: a flow housing providing at least one aperture through which blood to be measured flows the housing defining a space airtightly surrounding the aperture upstream thereof; a receiving means disposed downstream of said aperture to receive the blood which has flowed therethrough; and a suction tube adapted to carry a suction-induced flow of blood towards said aperture and arranged upstream of aperture and projecting into said space around the aperture upstream thereof, the downstream end of the suction tube being disposed in the vicinity of the aperture at such a spacing from the aperture that, with a given suction pressure, thrombus formation occurs in the aperture including an intermediate space between at least a portion of the peripheral surface of the suction of the suction tube, which portion directly adjoins said downstream end of the suction tube, and a housing wall portion which extends parallel thereto.

20. A device as set forth in claim 19 wherein the spacing between said peripheral surface of the suction tube and said wall portion extending parallel thereto, is no more than 2.0 mm.

21. A device as set forth in claim 20 wherein said spacing is approximately 0.5 mm.

* * * * *